(12) United States Patent
Katcha et al.

(10) Patent No.: US 7,593,502 B2
(45) Date of Patent: Sep. 22, 2009

(54) METHODS AND APPARATUS FOR FAST ROTATION SPEED SCANNERS

(75) Inventors: Jason Stuart Katcha, Whitefish Bay, WI (US); Bruce Matthew Dunham, Ithaca, NY (US); Robert Senzig, Germantown, WI (US); Jonathan Richard Schmidt, Wales, WI (US); Thomas Louis Toth, Brookfield, WI (US); David Michael Hoffman, New Berlin, WI (US); Phil E. Pearson, Jr., Hartland, WI (US); Jiang Hsieh, Brookfield, WI (US)

(73) Assignee: General Electric Company, Schenectady, NY (US)

( * ) Notice: Subject to any disclaimer, the term of this patent is extended or adjusted under 35 U.S.C. 154(b) by 259 days.

(21) Appl. No.: 11/580,489

(22) Filed: Oct. 13, 2006

(65) Prior Publication Data

US 2008/0095314 A1 Apr. 24, 2008

(51) Int. Cl.
*A61B 6/03* (2006.01)
(52) U.S. Cl. .................................. 378/4; 378/101
(58) Field of Classification Search ............ 378/4, 378/101
See application file for complete search history.

(56) References Cited

U.S. PATENT DOCUMENTS

| | | | |
|---|---|---|---|
| 4,672,528 A | 6/1987 | Park et al. | |
| 4,912,735 A | 3/1990 | Beer | |
| 5,510,622 A | 4/1996 | Hu et al. | |
| 5,608,771 A | 3/1997 | Steigerwald et al. | |
| 5,966,422 A * | 10/1999 | Dafni et al. | 378/9 |
| 6,055,450 A | 4/2000 | Ashburn | |
| 6,198,790 B1 * | 3/2001 | Pflaum | 378/9 |
| 6,256,369 B1 * | 7/2001 | Lai | 378/14 |
| 6,421,412 B1 | 7/2002 | Hsieh et al. | |
| 6,483,892 B1 * | 11/2002 | Wang et al. | 378/9 |
| 6,507,639 B1 * | 1/2003 | Popescu | 378/16 |
| 6,550,317 B2 | 4/2003 | Steinlage et al. | |

(Continued)

FOREIGN PATENT DOCUMENTS

DE 100 47 364 A1 4/2002

(Continued)

OTHER PUBLICATIONS

Novelty Search Report and Written Opinion regarding novelty and inventive step for Netherlands Application No. 1034519, dated Dec. 9, 2008, (15) pages.

*Primary Examiner*—Chih-Cheng G Kao
(74) *Attorney, Agent, or Firm*—Dean D. Small; The Small Patent Law Group (57) ABSTRACT

Methods and apparatus for an imaging system are provided. The imaging system includes a gantry having a stationary member coupled to a rotating member. The rotating member has an opened area proximate an axis about which the rotating member rotates. An x-ray source provided on the rotating member. An x-ray detector may be disposed on the rotating member and configured to receive x-rays from the x-ray source. A rotary transformer having circumferentially disposed primary and secondary windings may form part of a contactless power transfer system that rotates the rotatable portion of the gantry at very high speeds, the primary winding being disposed on the stationary member and the secondary winding being disposed on the rotating member.

42 Claims, 10 Drawing Sheets

U.S. PATENT DOCUMENTS

| | | |
|---|---|---|
| 6,597,758 B1 | 7/2003 | Rosner |
| 6,661,866 B1 * | 12/2003 | Limkeman et al. ............ 378/19 |
| 6,890,100 B2 | 5/2005 | Reznicek et al. |
| 6,895,077 B2 * | 5/2005 | Karellas et al. ............ 378/98.8 |
| 7,054,411 B2 | 5/2006 | Katcha et al. |
| 7,085,343 B2 * | 8/2006 | Shinno et al. .................. 378/9 |
| 2002/0176530 A1 | 11/2002 | Okumura et al. |
| 2004/0071256 A1 | 4/2004 | Hoffman |
| 2004/0136491 A1 | 7/2004 | Iatrou et al. |
| 2004/0234021 A1 * | 11/2004 | Hoffman ....................... 378/4 |
| 2004/0264642 A1 | 12/2004 | Katcha et al. |
| 2005/0089138 A1 * | 4/2005 | Toth et al. ..................... 378/20 |
| 2005/0147201 A1 * | 7/2005 | Hoffman ..................... 378/15 |
| 2005/0175143 A1 * | 8/2005 | Miyazaki et al. .............. 378/19 |
| 2005/0226380 A1 * | 10/2005 | Katcha et al. ............... 378/101 |
| 2007/0081624 A1 * | 4/2007 | Nabatame .................... 378/19 |

FOREIGN PATENT DOCUMENTS

| | | |
|---|---|---|
| DE | 102 45 578 A1 | 4/2004 |
| JP | 06169911 A | 6/1994 |
| WO | WO 91/00048 | 1/1991 |

* cited by examiner

METHODS AND APPARATUS FOR FAST ROTATION SPEED SCANNERS

BACKGROUND OF THE INVENTION

This invention generally relates to rotating imaging scanner systems and more particularly, to methods and apparatus for scanner systems having high rotational speeds.

High-voltage power transformers are used in a variety of applications, such as in baggage scanner systems, computed tomography (CT) systems and the like. CT systems are often used to obtain non-invasive sectional images of test objects, particularly internal images of human tissue for medical analysis and treatment. Current baggage scanner systems and CT systems position the test object, such as luggage or a patient, on a conveyor belt or table within a central aperture of a rotating frame which is supported by a stationary frame. The rotating frame includes an x-ray source and a detector array positioned on opposite sides of the aperture, both of which rotate around the test object being imaged. At each of several angular positions along the rotational path (also referred to as "projections"), the x-ray source emits a beam that passes through the test object, is attenuated by the test object, and is received by the detector array. The x-ray source utilizes high-voltage power to generate the x-ray beams.

Each detector element in the detector array produces a separate electrical signal indicative of the attenuated x-ray beam intensity. The electrical signals from all of the detector elements are collected and processed by circuitry mounted on the rotating frame to produce a projection data set at each gantry position or projection angle. Projection data sets are obtained from different gantry angles during one revolution of the x-ray source and detector array. The projection data sets are then processed by a computer to reconstruct the projection data sets into an image of a bag or a CT image of a patient.

The circuitry mounted on the rotating frame is powered by low-voltage power, while the x-ray source is powered by high-voltage power. Conventional rotating gantry based systems utilize a brush and slip ring mechanism to transfer power at a relatively low-voltage between the stationary and rotating portions of the gantry frame. The rotating gantry portion has an inverter and high-voltage tank mounted thereon and connected to the brush and slip ring mechanism. The inverter and high-voltage tank including transformer, rectifier, and filter capacitance components that step-up the voltage from the low-voltage, transferred through the brush and slip ring mechanism, to the high-voltage needed to drive the x-ray source. The transformer in the high-voltage tank produces a high-voltage AC signal which is converted to a high-voltage DC signal by rectifier circuits inside the high-voltage tank.

However, conventional rotating gantry based scanner systems have experienced certain disadvantages. The high-voltage tank and inverter on the rotating gantry portion increases the weight, volume and complexity of the system. Furthermore, the brush and slip ring mechanisms (which are typically used to carry appreciable current) are subject to reduced reliability, maintenance problems, and electrical noise generation, which interfere with sensitive electronics. As systems are developed that rotate faster, it becomes desirable to reduce the volume and weight of the rotating components.

A scanner apparatus and method are needed that address the above concerns and other problems experienced in the past.

BRIEF DESCRIPTION OF THE INVENTION

In one embodiment, an imaging system includes a gantry having a stationary member coupled to a rotating member, the rotating member having an opened area proximate an axis about which the rotating member rotates, an x-ray source provided on the rotating member, an x-ray detector disposed on the rotating member and configured to receive x-rays from the x-ray source, a resonant inverter, provided on the stationary member, to control an input voltage to the x-ray source and a rotary transformer having circumferentially disposed primary and secondary windings, the primary winding being disposed on the stationary member and the secondary winding being disposed on the rotating member, the rotary transformer including a leakage inductance that is coupled to the resonant inverter to form a resonant network.

In another embodiment, an imaging system may include a gantry having a stationary member coupled to a rotating member. The rotating member may have an opened area proximate an axis about which the rotating member rotates. The imaging system also includes a plurality of x-ray sources provided on the rotating member, a first x-ray source including an x-ray tube of a first type and a second x-ray source including an x-ray tube of a second type wherein the first and second types are different, a resonant inverter, provided on the stationary member, to control an input voltage to the x-ray source. The imaging system further includes a plurality of x-ray detectors disposed on the rotating member and configured to receive x-rays from at least one of the x-ray sources, a first x-ray detector including an x-ray detector of a first type and a second x-ray detector including an x-ray detector of a second type wherein the first and second types are different, and a rotary transformer having circumferentially disposed primary and secondary windings, the primary winding being disposed on the stationary member and the secondary winding being disposed on the rotating member, resonant network is formed by a capacitor, provided along an output leg of the inventor, coupled in series with the leakage inductance of the rotary transformer.

In yet another embodiment, an imaging system gantry mechanism may include a stationary member and a rotating member that is rotatably coupled to the stationary member. The rotating member may have an opened area proximate an axis about which the rotating member rotates. The imaging system gantry mechanism may further include an x-ray source provided on the rotating member, an x-ray detector disposed on the rotating member and configured to receive x-rays from the x-ray source, and a rotary transformer having circumferentially disposed primary and secondary windings wherein the primary winding are disposed on the stationary member and the secondary winding are disposed on the rotating member. The secondary windings are coupled to a high voltage tank that is distributed about an outer periphery of the rotating member.

In still another embodiment, an imaging system gantry mechanism includes a stationary member, a rotating member rotatably coupled to the stationary member, the rotating member having an opened area proximate an axis about which the rotating member rotates, an x-ray source provided on the rotating member, and an x-ray detector disposed on the rotating member and configured to receive x-rays from the x-ray source. The imaging system gantry mechanism further includes a rotary transformer having a circumferentially disposed primary winding and a plurality of circumferentially disposed secondary windings that are complementary to the primary winding. The primary windings are disposed on the stationary member and the secondary windings are disposed on the rotating member. Each secondary winding provides power to a respective rotary member subsystem. Each secondary winding is coupled to a respective high voltage tank that is distributed about an outer periphery of the rotating member to carry power to the respective rotary member subsystem.

DETAILED DESCRIPTION OF THE INVENTION

Figure 1:
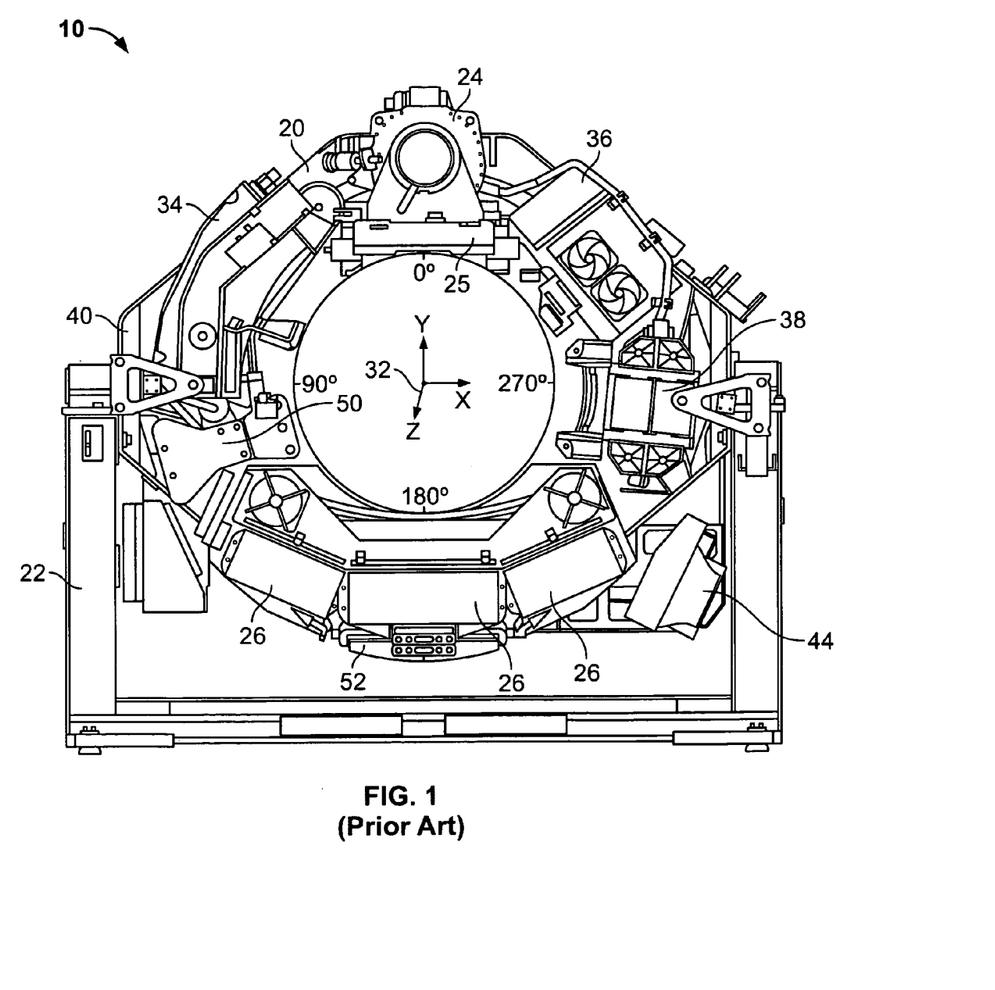
FIG. 1 is a front view of an exemplary imaging system gantry mechanism, with covers removed, including a rotating member and stationary base member.

FIG. 1 is a front view of an exemplary gantry mechanism 10, with covers removed, including a rotating base member 20 and stationary base member 22. An x-ray tube 24 and collimator 25 are positioned on rotating base member 20 together with a detector plate member 26. A patient or other object (not shown) is positioned on a table member (not shown) and moved along a Z-axis 32 which is the axis of rotation of rotating base member 20. X-ray tube member 24 and detector plate member 26 are positioned opposite one another on rotating base member 20 and x-ray images of the patient or object on the table member are made as the table member moves through the central opening of the gantry mechanism 10.

Rotating base member 20 includes additional components spaced circumferentially thereabout. These may include a heat exchanger 34, a high voltage generator 36, and a high voltage tank 38. Also, as is common with CT systems, an axial bearing and slip ring (not shown) are attached to the rotating base member 20. A bearing bracket 40 is used to attach the axial bearing to the stationary base member 22. Electrical power is supplied to the electrical components on rotating base member 20 through the slip ring and slip ring brushes as typical in CT systems. An axial motor assembly 44 is utilized to rotate the rotating base member 20 relative to stationary base member 22.

The relative positions of the components on a rotating base member 20 are indicated by degrees from the twelve o'clock position as shown in FIG. 1, where the zero degree point is indicated at the twelve o'clock position. As illustrated, the degrees are measured counter-clockwise when the gantry member is viewed from the front. Thus, the 90° position is loaded at the nine o'clock position, and the 180° position is located at the six o'clock position, etc.

Due to the weight of the various components, which are positioned on the rotating base member 20, and their relative positions, the gantry member is typically unbalanced when it rotates. This imbalance is both in the X-axis and Y-axes directions, as well as the Z-axis direction. To counter such imbalance, balance weight systems are utilized at two pre-selected sites 50 and 52.

Imbalance of rotating base member 20 results in an oscillatory motion of the entire gantry at a frequency of once per revolution. This motion is detrimental to image quality, as it can generate artifacts when the motion is increased above some threshold. At increased rotating speeds the oscillatory motion may generate forces that can exceed failure thresholds of some components resulting in increased maintenance requirements of system 10.

Figure 2:
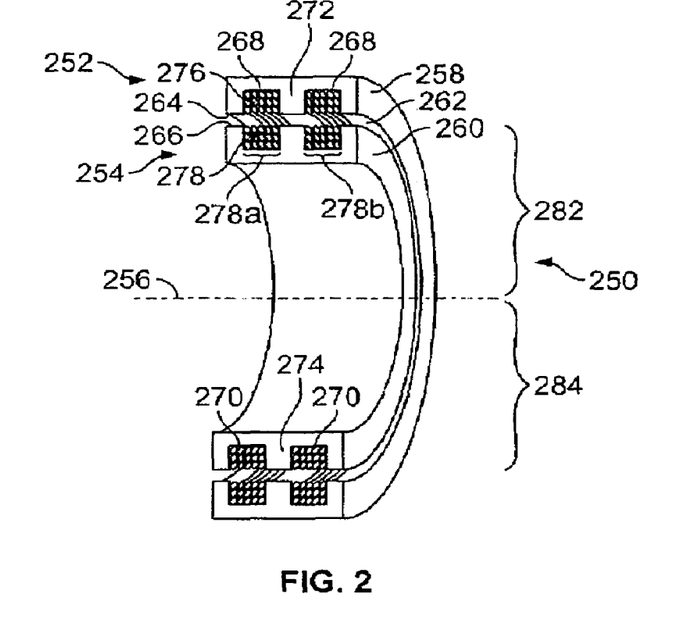
FIG. 2 illustrates a contactless power transfer system configured to replace the slip rings and brushes of conventional CT systems.

FIG. 2 illustrates a contactless power transfer system 250 configured to replace the slip rings and brushes of conventional CT systems. The system 250 includes a stationary member 252 and a rotating member 254 located proximate one another and in a concentric arrangement about axis 256. The rotating member 254 rotates about axis 256 relative to the stationary member 252. By way of example, the stationary member 252 may simply represent a stator, while the rotating member 254 may represent a rotor, both of which may be coupled to a common framework, such as a gantry. The stationary member 252 has a stationary core 258, while the rotating member 254 has a rotating core 260. The stationary and rotating cores 258 and 260 have corresponding inner and outer surfaces 264 and 266, respectively. The inner and outer surfaces 264 and 266 are separated by an air gap 262, are directed toward one another and rotate in close proximity to one another.

The stationary and rotating cores 258 and 260 have E-shaped cross sections aligned with, opening toward one another, and extending in a cylindrical or tubular manner about the axis 256. The E-shaped cross-section in the stationary core 258 includes parallel winding slots 268 cut in the inner surface 264 and separated by a middle leg 272. The winding slots 268 and middle leg 272 face inward toward, and extend in a circumferential direction about, the axis 256. The rotating core 260 includes parallel winding slots 270 cut in the outer surface 266 and separated by a middle leg 274. The winding slots 270 and middle leg 274 face outward away from, and extend in a circumferential direction about, the axis 256.

The stationary core 258 receives a primary winding 276 that is provided within the winding slots 268 and wrapped about the middle leg 272. The primary winding 276 loops about the complete circumference of the inner surface 264 within the winding slots 268. The primary winding 276 is wound in one direction in one of winding slots 268 and loops back in the opposite direction in the other of winding slots 268. The rotating core 260 receives a secondary winding 278 that are provided within the winding slots 270 and wrapped about segments of the middle leg 274. The secondary winding 278 is divided into separate sub-windings that loop or wrap in opposite directions within the secondary winding slots 270. The rotating core 260 and secondary windings 278 are divided into arcuate sections 282 and 284. Each arcuate section 282 and 284 includes a separate and independent secondary sub-winding. Each secondary sub-winding includes a forward path 278a and a return path 278b. The forward and return paths 278a and 278b are spaced a substantially equal distance from the primary winding 276. The distance between the primary winding 276 and forward and return paths 278a and 278b corresponds to a thickness or width of the air gap 262. The forward and return paths 278a and 278b are arranged in a common curved or cylindrical plane defined by and following a contour of the outer surface 266 of the rotating core 260. In the example of FIG. 1, half of the stationary rotating members 252 and 254 are shown, but it is understood that the other similarly structured. Thus, in the example of FIG. 1, the rotating core 260 includes four arcuate sections, each comprising approximately 90° of the rotating core 260.

The external magnetic fields are very small, thereby limiting magnetic and electrical interference with rotating electronics including the data acquisition system. The magnetic fields are small at some distance from the cores due to the magnetic field cancellation between the primary and secondary windings 276 and 278. The magnetic field cancellation in the E-shaped core configuration is achieved by locating the return path of the primary and each secondary sub-windings immediately adjacent one another, and the planes (flat or curved) formed by the primary and secondary windings face each other separated only by the air gap 262.

Figure 3:
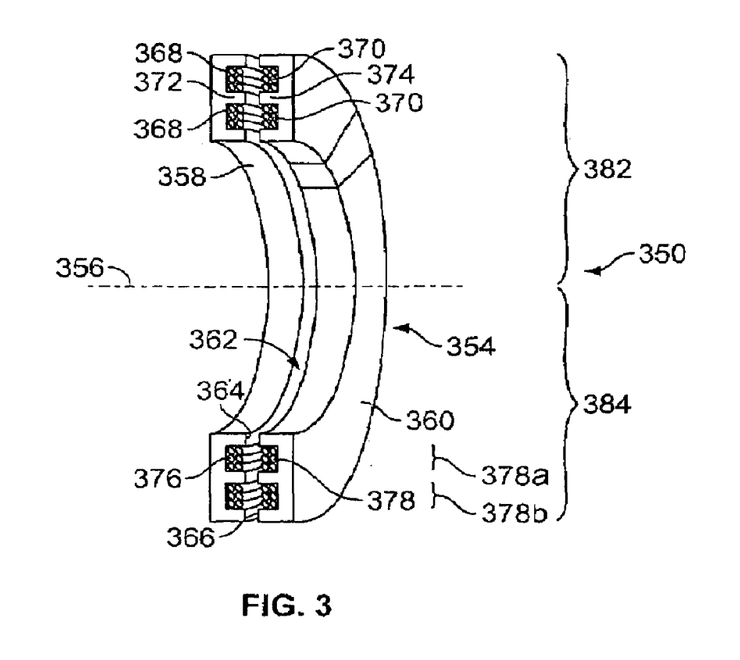
FIG. 3 illustrates a contactless power transfer system formed in accordance with an alternative embodiment.

FIG. 3 illustrates a contactless power transfer system 350 constructed in accordance with an alternative embodiment. The system 350 includes a stationary member 352 and a rotating member 354 located proximate one another and in facing parallel planes extending perpendicular to an axis 356. The rotating member 354 rotates relative to the stationary member 352 about axis 356 and within a plane aligned parallel to a plane containing the stationary member 352. By way of example, the stationary member 352 may simply represent a stator, while the rotating member 354 may represent a rotor. The stationary member 352 has a stationary core 358, while the rotating member 354 has a rotating core 360. The stationary and rotating cores 358 and 360 are separated by an air gap 362 and have open facing sides 364 and 366, respectively that are directed toward one another and rotate in close proximity to one another. The stationary and rotating cores 358 and 360 extend along corresponding parallel planes.

The stationary and rotating cores 358 and 360 have E-shaped cross sections aligned with and facing one another. The E-shaped cross-section in the stationary core 358 includes parallel winding slots 368 cut in the side 364 and separated by a middle leg 372. The winding slots 368 and middle leg 372 extend about the axis 356 and lie within the plane containing the stationary core 358. The rotating core 360 includes parallel winding slots 370 cut in the side 366 and separated by a middle leg 374. The winding slots 370 and middle leg 374 extend about the axis 356 and lie within the plane containing the stationary core 360.

The stationary core 358 receives a primary winding 376 that is provided within the winding slots 368 and wrapped about the middle leg 372. The primary winding 376 extends along the side 364 about the axis 356 and is aligned with the plane containing the stationary core 358. The primary winding 376 is wound in one direction in one of winding slots 368 and loops back to return in the opposite direction in the other of winding slots 368. The rotating core 360 receives secondary winding 378 that is provided within the winding slots 370 and wrapped about segments of the middle leg 374. The secondary winding 378 are wound in opposite directions, to the primary winding 376, in the secondary winding slots 370. The rotating core 360 and secondary windings 378 are divided into arcuate sections 382 and 384. Each arcuate section 382 and 384 includes a separate and independent secondary sub-winding (as will be described more below). Each secondary sub-winding 378 includes a forward path 378a and a return path 378b. The forward and return paths 378a and 378b are spaced a substantially equal distance (corresponding to the width of the air gap 362) from the primary winding 376. The forward and return paths 378a and 378b are aligned in a common flat plane defined by and following the side 366 of the rotating core 360.

As explained above in connection with FIG. 2, the external magnetic fields are very small at some distance from the rotating core 360. In the configuration of FIG. 3, the magnetic fields are small at some distance from the rotating cores due to the magnetic field cancellation between the primary and secondary windings 376 and 378. The magnetic field cancellation in the E-core configuration is quite substantial given that the configuration locates the return path of the primary and secondary windings immediately adjacent one another and separated only by the air gap 362.

Figure 4:
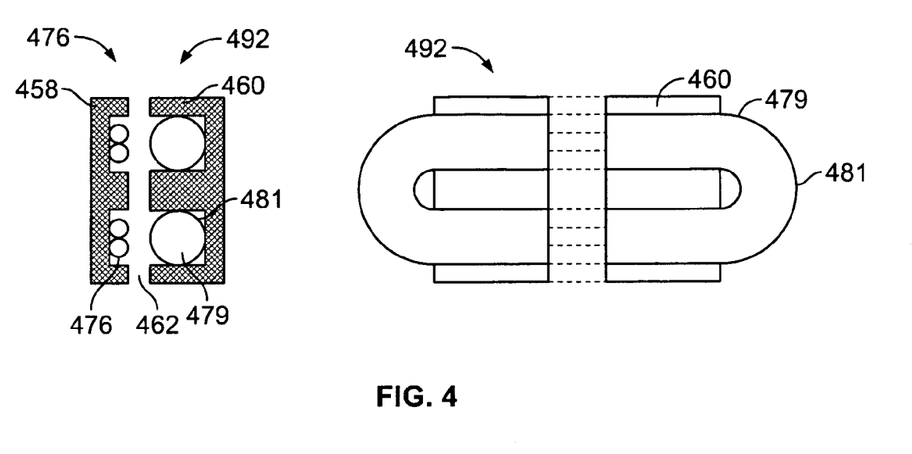
FIG. 4 illustrates a cross-sectional layout of a simplified primary winding and a single secondary sub-winding arranged in parallel planes, as well as a front view of the secondary sub-winding.

FIG. 4 illustrates a cross-sectional layout of a simplified primary winding 476 and a single secondary sub-winding 492 arranged in parallel planes, as well as a front view of the secondary sub-winding 492. The secondary sub-winding 492 is held in an arcuate portion of a rotating core 460 in close proximity to the primary winding 476. The secondary winding 478 includes a conductive wire 479 surrounded by high-voltage insulation 481. One or more loops of the wire 479 and insulation 481 may form the sub-winding 492. As the rotating core 460 rotates relative to the stationary core 458, the primary winding 476 and secondary sub-winding 492 remain in close proximity to one another, separated only by the air gap 462.

Figure 5:
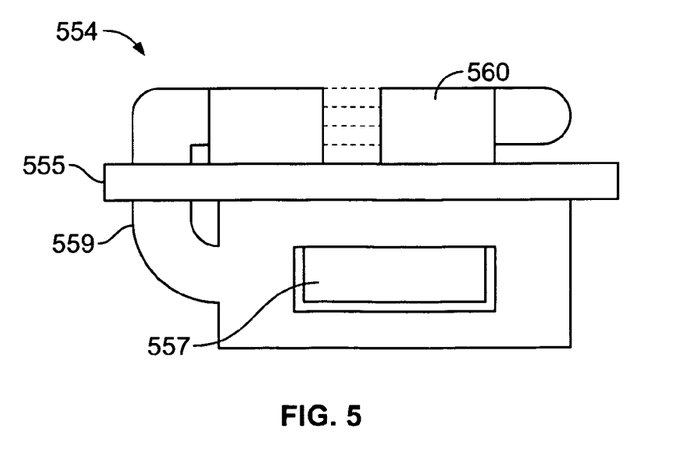
FIG. 5 illustrates a side view of a rotating member that includes a platter with the rotating core mounted thereon.

FIG. 5 illustrates a side view of a rotating member 554 that includes a platter 555 with the rotating core 560 mounted thereon. The rotating core 560 is provided on a first side of the platter 555, while a signal conditioning module 557 is provided on the opposite side of the platter 555. The signal conditioning module 557 is joined to the secondary sub-winding 492 (shown in FIG. 4) through sub-winding output leads 559. By way of example, the voltage provided over the sub-winding output leads 559 may be 40 kV AC, which is then converted by the signal conditioning module 557 to 40 kV DC.

Figure 6:
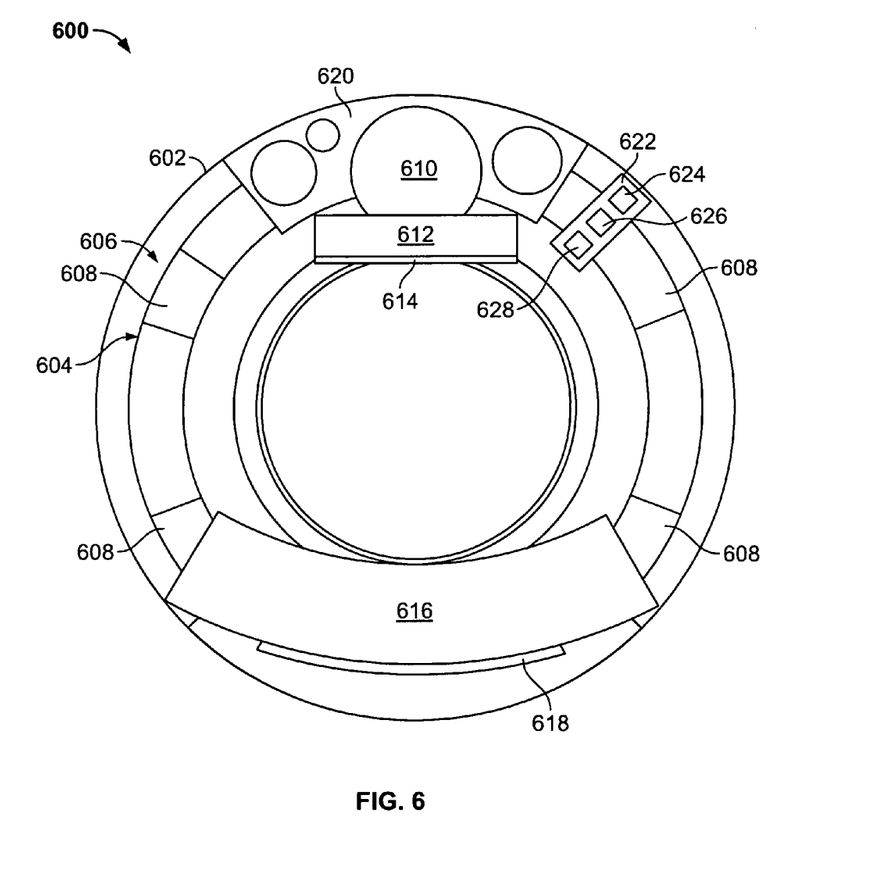
FIG. 6 is a schematic front view of a gantry mechanism constructed in accordance with an exemplary embodiment.

FIG. 6 is a schematic front view of a gantry mechanism 600 constructed in accordance with an exemplary embodiment. Gantry mechanism 600 includes a rotatable member 602 that also includes a rotating core 604 of a contactless power transfer system 606 (only the rotating portion is illustrated in FIG. 6). One or more rectifiers 608 are coupled to rotating core 604 at positions distributed circumferentially about rotatable member 602. Spacing the rectifiers about rotatable member 602 permits a relatively even distribution of weight about rotatable member 602, which in turn facilitates reducing imbalance in a fully assembled rotatable member 602. Circumferentially spacing a plurality of rectifiers 608 about rotatable member 602 also permits positioning rectifiers 608 closer to components that use the power produced by rectifiers 608. The rotatable member 602 exhibits a leakage inductance that is used as part of a resonant network of a resonant inverter.

In an exemplary embodiment, rotatable member 602 includes an x-ray tube 610 and an associated pre-patient collimator 612 that in various embodiments also includes an energy filter 614. A detector 616 is associated with x-ray tube 610 and is spaced circumferentially approximately 180° along rotatable member 602 from x-ray tube 610. Detector 616 is configured to receive radiation emitted from x-ray tube 610, a portion of which passes through an object being examined and convert the received radiation into data relating to an attenuation of the radiation that has passed through the object. Data acquisition electronics 618 are coupled to detector 616 to convert the data into signals that can be transmitted to a processor for analysis and image generation.

A heat exchanger 620 includes apparatus configured to remove heat from the fluid circulating in rotatable member 602. Heat exchanger 620 may also be configured to condition the fluid to facilitate operation of the components associated with x-ray tube 610, detector 616, and rotatable member 602.

An auxiliary panel 622 may be mounted to rotatable member 602 proximate x-ray tube 610 and may contain a rotor control section 624 and a filament drive section 626, and an auxiliary section 628. Rotor control section includes the control elements for controlling the operation of the x-ray tube rotor. Filament drive section 626 includes the controls elements for controlling the voltage supplied to the x-ray tube filament, and auxiliary section 628 includes elements for controlling other components positioned on rotatable member 602 such as a focal spot wobble amplifier and communications hardware, and systems to provide real-time feedback to x-ray tube 610 and filament drive section 626 using for example, but not limited to a real-time dosimeter, a scatter detector, and an x-ray detector element. Auxiliary section 628 also includes elements future expansion and features that may be retro-fit onto rotatable member 602.

In practice, an exemplary embodiment of rotatable member 602 may have less physical hardware than a comparable prior art rotating base member 20 (shown in FIG. 1). The use of contactless power transfer system 606 permits elimination or relocation of inverter or high voltage generator 36 and high voltage tank 38 (both shown in FIG. 1) from rotatable member 602 to a stationary member (not shown) associated with rotatable member 602. For example, when an inverter and/or high voltage tank are used, they could be provided on the stationary member, such as stationary base member 22 (FIG. 1) or stationary member 252 (FIG. 2). Additionally, other power supply modules required in prior art rotating base member 20 (shown in FIG. 1) are eliminated due to a separate power supply channel of contactless power transfer system 606 supplying power for the respective components. Because rotatable member 602 includes less mass than rotating base member 20, rotatable member 602 is less susceptible to imbalance forces that are large enough to damage components even at high rotational speeds than used previously in imaging systems.

Figure 7:
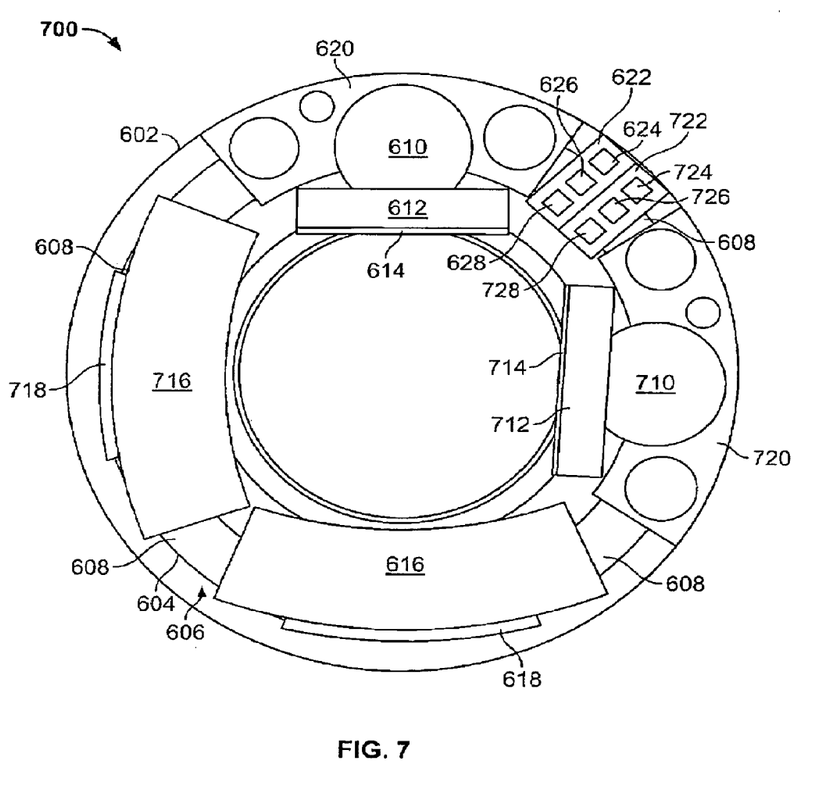
FIG. 7 is a schematic front view of a gantry mechanism constructed in accordance with another exemplary embodiment.

FIG. 7 is a schematic front view of a gantry mechanism 700 in accordance with another exemplary embodiment of the present invention. Gantry mechanism 700 is substantially similar to gantry mechanism 600, (shown in FIG. 6) and components of gantry mechanism 700 that are identical to components of gantry mechanism 600 are identified in FIG. 7 using the same reference numerals used in FIG. 6. Gantry mechanism 700 includes rotatable member 602 that also includes rotating core 604. One or more rectifiers 608 are coupled to rotating core 604 at positions distributed circumferentially about rotatable member 602.

In the exemplary embodiment, rotatable member 602 includes x-ray tube 610 and a second x-ray tube 710. Each x-ray tube 710 typically includes an associated pre-patient collimator 612 and 712, respectively, that in various embodiments also includes an associated energy filter 614 and 714. Radiation detector 616 is associated with x-ray tube 610 and a second radiation detector 716 is associated with x-ray tube 710. Each of radiation detectors 616 and 716 are spaced circumferentially approximately 180° along rotatable member 602 from its respective x-ray tube 610 and 710. Data acquisition electronics 618 and 718 are coupled to detectors 616 and 716, respectively, to convert attenuation data received from detectors 616 and 716 into signals that can be transmitted to a processor for analysis and image generation. Heat exchangers 620 and 720 are configured to remove heat from the fluid circulating in rotatable member 602. Heat exchangers 620 and 720 may also be configured to condition the fluid to facilitate operation of the components associated with x-ray tubes 610 and 710, detectors 616 and 716, and rotatable member 602. Conditioning may include, but is not limited to, heating, cooling, dehumidifying, humidifying, and filtering.

Auxiliary panels 622 and 722 are mounted to rotatable member 602 proximate each associated x-ray tube 610 and 710. Auxiliary panels 622 and 722 each include a rotor control section 624 and 724, a filament drive section 626 and 726, and an auxiliary section 628 and 728. Rotor control sections 624 and 724 include the control elements for controlling the operation of the respective x-ray tube rotor. Filament drive sections 626 and 726 include the control elements for controlling the voltage supplied to the respective x-ray tube filament, and auxiliary sections 628 and 728 include elements for controlling other components positioned on rotatable member 602 and for future expansion and features that may be retro-fit onto rotatable member 602.

In practice, an exemplary embodiment of rotatable member 602 is able to support installation of two x-ray tubes and two radiation detectors because the use of contactless power transfer system 606 permits elimination or relocation of high voltage generator 36 and high voltage tank 38 (both shown in FIG. 1) from rotatable member 602 to the stationary member (not shown) associated with rotatable member 602. Additionally, other power supply modules required in prior art rotating base member 20 (shown in FIG. 1) are eliminated due to a separate power supply channel of contactless power transfer system 606 supplying power for the respective components.

Figure 8:
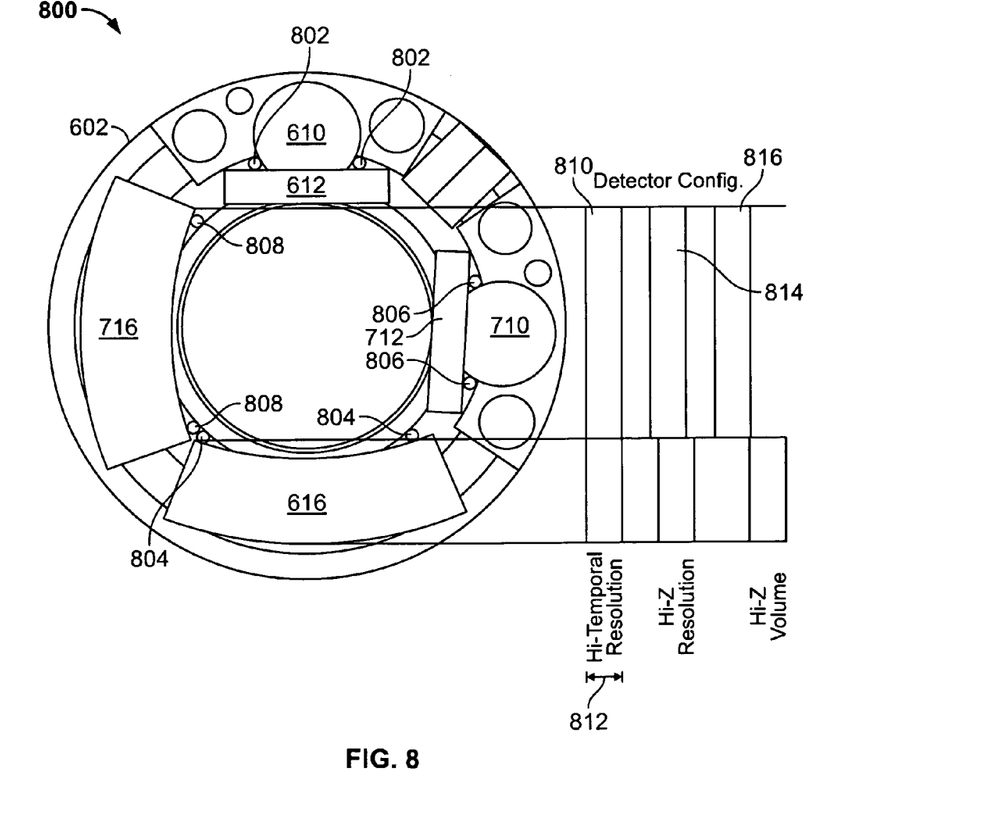
FIG. 8 is a schematic front view of a gantry mechanism constructed in accordance with another exemplary.

FIG. 8 is a schematic front view of a gantry mechanism 800 constructed in accordance with another exemplary embodiment. Gantry mechanism 800 is substantially similar to gantry mechanism 700, (shown in FIG. 7) and components of gantry mechanism 800 that are identical to components of gantry mechanism 700 are identified in FIG. 8 using the same reference numerals used in FIG. 7.

In an exemplary embodiment, gantry mechanism 800 includes x-ray tubes 610 and 710 and associated collimators 612 and 712, respectively. Detectors 616 and 716 are spaced approximately 180° about a circumference of rotatable member 602 with respect to x-ray tubes 610 and 710, respectively. Although, typically, detectors 616 and 716 and x-ray tubes 610 and 710 would be aligned in the z direction in other embodiments, in this exemplary embodiment, each of detectors 616 and 716 and x-ray tubes 610 and 710 are coupled to actuators 802, 804, 806, and 808 that permit movement of one or more of detectors 616 and 716 and x-ray tubes 610 and 710 to be translated in the z direction. Specifically, actuator 802 supports x-ray tube 610 on rotatable member 602 and provides a motive force and alignment for x-ray tube 610 when translating from a first position in the z-direction and a second position in the z-direction. Each of actuators 804, 806, and 808 also support and provide a motive force and alignment for detector 616, x-ray tube 710, and detector 716, respectively. Actuators 802, 804, 806, and 808 may comprise a piston and cylinder actuator that is movable using hydraulics or pneumatics. Alternatively, actuators 802, 804, 806, and 808 may comprise a lead screw assembly and a drive motor.

Actuators 802, 804, 806, and 808 are used to move one or more of detectors 616 and 716 and x-ray tubes 610 and 710 in a z-direction such that all of the detectors 616 and 716 and x-ray tubes 610 and 710 are aligned in the z-direction or offset with respect to each other in the z-direction. When one or more of detectors 616 and 716 and x-ray tubes 610 and 710 are aligned with respect to each other, illustrated at 810, sampling of the radiation passing through the object under examination occurs with greater temporal resolution. The attenuation data is collected twice as fast as when only one detector is available to collect data in each revolution. When detector 616 and detector 716 are offset with respect to each other in the z-direction by a distance 812 that is less than the z-dimension of the detectors, as illustrated at 814, the attenuation data is collected at a resolution greater than when only one detector is used per revolution. Similarly, when detector 616 and detector 716 are offset with respect to each other in the z-direction by a distance that is equal to the z-dimension of the detectors, as illustrated at 816, the attenuation data is collected over a volume that is twice as great per revolution as when a single detector is used. In the exemplary embodiment, actuators 802, 804, 806, and 808 are configured to move detectors 616 and 716 and x-ray tubes 610 and 710 on the fly, that is, during a scan of an object, an operator may initiate a control signal to drive actuators 802, 804, 806, and 808. Driving actuators 802, 804, 806, and 808 to a different position also translates detectors 616 and 716 and x-ray tubes 610 and 710 to a different location with respect to each other. For example, during a portion of a scan where detailed information is not required, detectors 616 and 716 and x-ray tubes 610 and 710 may be aligned offset with respect to each other by an amount equal to distance 812. Such an alignment permits relatively high volume scanning at relatively low temporal resolution and relatively low spatial resolution in the z-direction. During a portion of the scan where detailed information is required, detectors 616 and 716 and x-ray tubes 610 and 710 may be aligned offset with respect to each other by an amount less than distance 812. Such an alignment permits scanning with relatively high spatial resolution in the z-direction at relatively low temporal resolution and at relatively low z-direction volume.

In an alternative embodiment, detectors 616 and 716 and x-ray tubes 610 and 710 are aligned offset with respect to each other by an amount greater than distance 812 to permit extended volume sampling during a scan. Data from areas missed during each revolution are then calculated from data received from portions of detectors 616 and 716 adjacent the missing areas. Additionally, x-ray tube 610 and detector 616 and/or x-ray tube 710 and detector 716 may be aligned offset from each other in the z-direction. In a further embodiment, actuators 802 and 806 are configured to tilt x-ray tubes 610 and 710 respectively, such that an x-ray beam generated by x-ray tubes 610 and 710 impinges detectors 616 and 716 obliquely rather than orthogonally.

Figure 9:
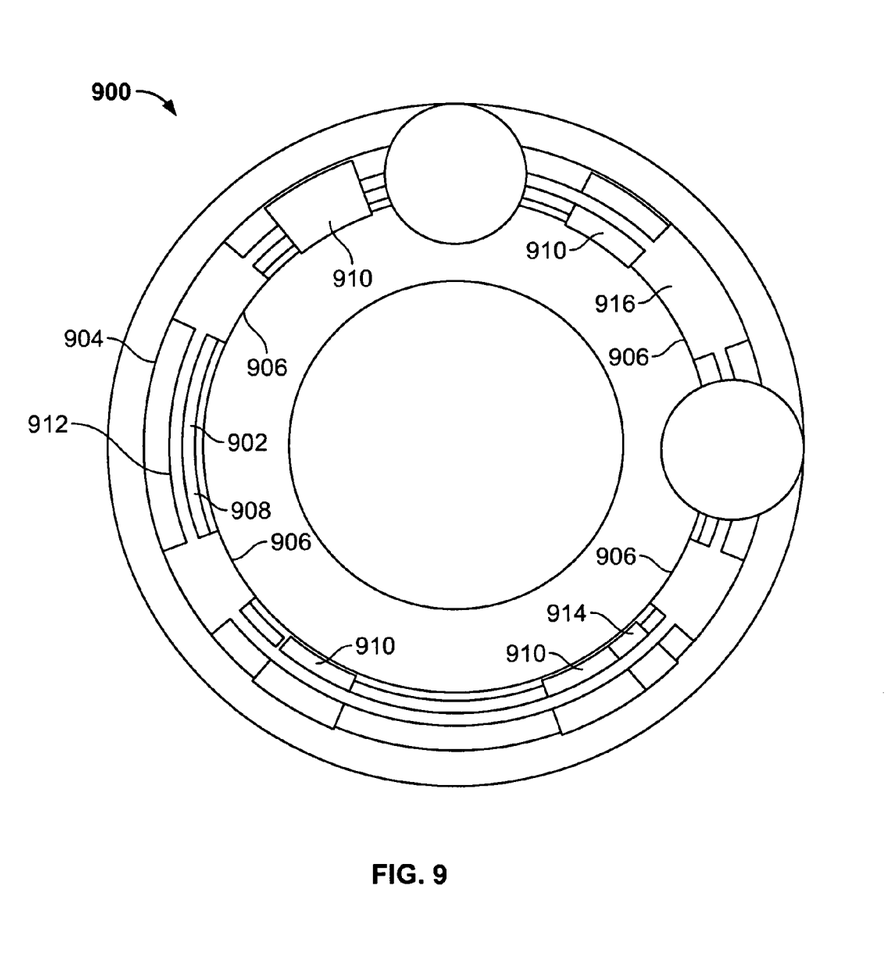
FIG. 9 is a schematic front view of a gantry mechanism constructed in accordance with another exemplary.

FIG. 9 is a schematic front view of a gantry mechanism 900 in accordance with another exemplary embodiment. In this embodiment gantry mechanism 900 includes multiple rotary transformers represented as a radially inner rotary transformer 902 and a radially outer rotary transformer 904. The rotary transformers 902 and 904 are each coupled to respective distributed high voltage tanks for scalable power and independent control of each x-ray tube voltage and current. One or more rectifiers 906 are coupled to windings 908 of inner rotary transformer 902 and rectifiers 910 are coupled to windings 912 of outer rotary transformer 904. A filament transformer 914 and 916 is coupled to windings 908 and 912 respectively. Filament transformers 914 and 916 are generally coupled between the rectifier closest to the respective tube and the tube.

The independent nature of the separate rotary transformers 902 and 904 permits scalability of the power needs of the various components located on gantry mechanism 900. For example, two rotary transformers may be used to supply power to a single x-ray tube, such as a high power tube. Selection of a type of tube may be dependent on a scan that is to be performed. For example, a low power micro-focus x-ray tube and a respective high resolution detector may be used in conjunction to provide high resolution scanning. A relatively high power tube and a respective energy discriminating detector may be used for another scan protocol.

Figure 10:
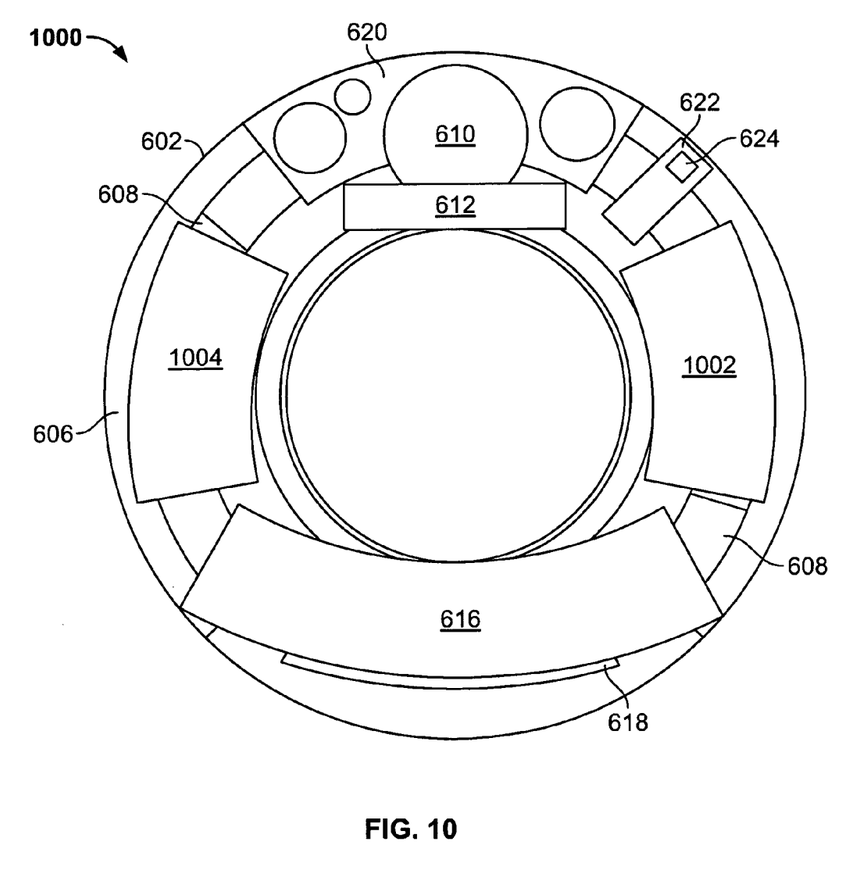
FIG. 10 is a schematic front view of a gantry mechanism constructed in accordance with yet another exemplary.

FIG. 10 is a schematic front view of a gantry mechanism 1000 in accordance with yet another exemplary embodiment. Gantry mechanism 1000 is substantially similar to gantry mechanism 600, (shown in FIG. 6) and components of gantry mechanism 1000 that are identical to components of gantry mechanism 600 are identified in FIG. 10 using the same reference numerals used in FIG. 6. Gantry mechanism 1000 includes rotatable member 602 that also includes rotating core 604 of contactless power transfer system 606. One or more rectifiers 608 are coupled to rotating core 604 at positions distributed circumferentially about rotatable member 602. Spacing the rectifiers about rotatable member 602 permits a relatively even distribution of weight about rotatable member 602, which in turn facilitates reducing imbalance in a fully assembled rotatable member 602. Circumferentially spacing rectifiers 608 about rotatable member 602 also permits positioning rectifiers 608 closer to components that use the power produced by rectifiers 608.

In the exemplary embodiment, rotatable member 602 includes an x-ray tube 610 and an associated pre-patient collimator 612 that in various embodiments also includes an energy filter 614. Detector 616 is associated with x-ray tube 610 and is spaced circumferentially approximately 180° along rotatable member 602 from x-ray tube 610. Detector 616 is configured to receive radiation emitted from x-ray tube 610, a portion of which passes through an object being examined and convert the received radiation into data relating to an attenuation of the radiation that has passed through the object. Data acquisition electronics 618 are coupled to detector 616 to convert the data into signals that can be transmitted to a processor for analysis and image generation.

Heat exchanger 620 includes apparatus configured to remove heat from the fluid circulating in rotatable member 602. Heat exchanger 620 may also be configured to condition the fluid to facilitate operation of the components associated with x-ray tube 610, detector 616, and rotatable member 602.

An auxiliary panel 622 is mounted to rotatable member 602 proximate x-ray tube 610 and contains rotor control section 624 and filament drive section 626, and an auxiliary section 628. Rotor control section includes the control elements for controlling the operation of the x-ray tube rotor. Filament drive section 626 includes the controls elements for controlling the voltage supplied to the x-ray tube filament, and auxiliary section 628 includes elements for controlling other components positioned on rotatable member 602 such as the focal spot wobble amplifier and communications hardware, and systems to provide real-time feedback to x-ray tube 610 and filament drive section 626 using for example, but not limited to the real-time dosimeter, the scatter detector, and the x-ray detector element. Auxiliary section 628 also includes elements future expansion and features that may be retro-fit onto rotatable member 602.

In the exemplary embodiment, gantry mechanism 1000 also includes a first gamma camera or positron emission tomography (PET) detector 1002 and a second gamma camera or positron emission tomography (PET) detector 1004 spaced circumferentially about gantry mechanism 1000. Detectors 1002 and 1004 are configured to detect gamma emissions from a radiopharmaceutical administered to a patient positioned between detectors 1002 and 1004. Detectors 1002 and 1004 may be used for single positron emission computed tomography (SPECT) imaging, PET imaging and other nuclear medicine imaging modalities. In the exemplary embodiment, detectors 1002 and 1004 are powered from separate rotary transformers or alternatively the same rotary transformer included on gantry mechanism 1000. In the exemplary embodiment, a centerline in the z-direction of detectors 1002 and 1004 are aligned with a centerline in the z-direction of detector 616. Such alignment provides coincident imaging planes for both modalities a multimodality imaging system with inherent registration of images from each modality.

In operation, gantry mechanism is rotated at a first rotation speed that permits acquisition of computed tomography (CT) data sequentially with emission data acquired at a second rotation speed, which is generally relatively slower than the first rotational speed. In an alternative embodiment, CT and emission data are acquired simultaneously at the same rotational speed. Emission data includes PET data, SPECT data, and other nuclear imaging data.

Figure 11:
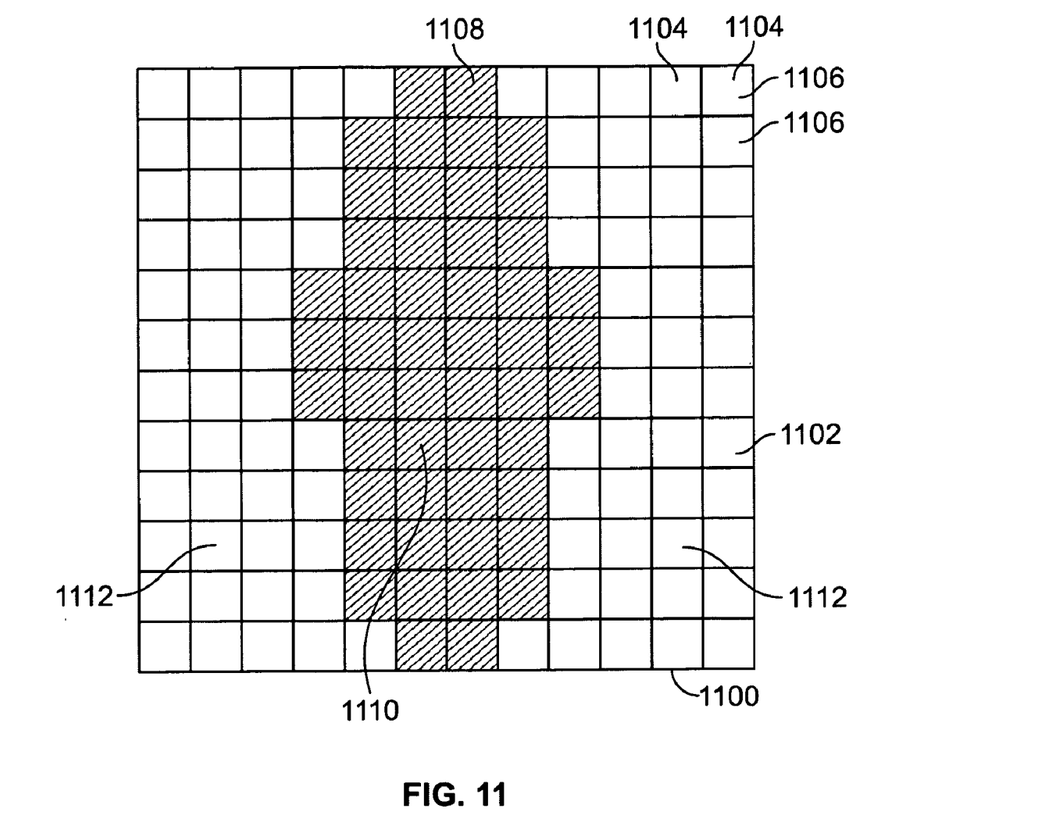
FIG. 11 is a schematic view of an exemplary detector that may be used with the various embodiments of the gantry mechanism in accordance with an embodiment.

FIG. 11 is a schematic view of an exemplary detector 1100 that may be used with the various embodiments of the gantry mechanism in accordance with an embodiment. Detector 1100 includes a radially inner surface 1102 comprising a plurality of pixilated detector elements 1104. Each element includes structural characteristics that determine its sensitivity to incident radiation and its ability to localize the area of incidence, for example, its resolution. In the exemplary embodiment, detector 1100 includes elements 1106 that are configured for low resolution imaging and elements 1108 that are configured for high resolution imaging. Elements 1106 and 1108 are configured for their respective resolution imaging using a pixel size, in which smaller sized pixels are used for high resolution imaging and larger sized pixels are used for low resolution imaging. In an alternative embodiment, a mask or post patient collimator is used to provide high and low resolution capabilities to elements 1108 and 1106 respectively. The high and low resolution elements 1108 and 1106 are grouped into high and low resolution areas 1110 and 1112 respectively. Accordingly, detector 1100 may be used with a radiation source such as an x-ray tube (not shown) for imaging a specific area of interest of an object in high resolution with the rest of the image imaged in relatively low resolution.

Figure 12:
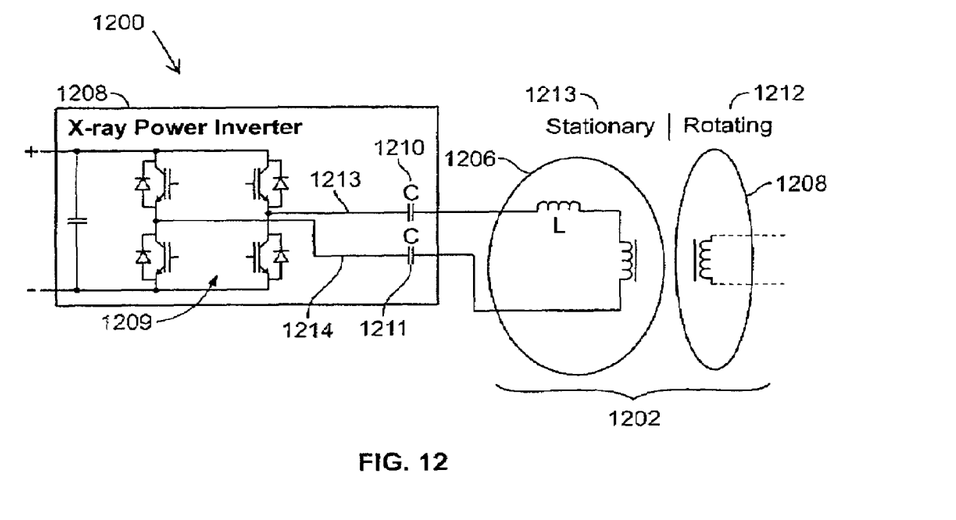
FIG. 12 is a schematic view of a contactless power transfer system in accordance with an embodiment.

FIG. 12 is a schematic diagram of a multichannel, contactless power transfer system 1200. The system 1200 may be mechanically structured in accordance with the arrangements of FIG. 2 or 3, or in an alternative manner. Power from the stationary frame 1213 is transferred to the rotating frame 1212 by means of a multichannel, rotary transformer 1202. The rotary transformer 1202 transfers the primary x-ray generation power through one or more channels. Power conversion devices (such as inverter 1208) can be disposed on the stationary frame 1213. The inverter 1208 includes four insulated gate bipolar (IBT) transistor switches 1209 that are used to produce high frequency current and voltage. The inverter 1208 includes a pair of output legs 1213 and 1214 on the AC output side of the inverter 1208. The output legs 1213 and 1214 each include one or more resonant capacitors 1210 and 1211. The capacitors 1210 and 1211 form a series resonant circuit with the leakage inductance component formed within the rotary transformer 1202. The rotary transformer 1202 is configured to include an x-ray power primary winding 1206 and secondary winding 1208. Optionally, multiple secondary windings (having equal or different numbers of turns) may be integrated into the rotary transformer 1202 to provide the various DC voltages desired (e.g., 600 VDC, 48 VDC, 24 VDC, etc.). The rotary transformer 1202 includes a leakage inductance, L, which serves as the resonant inductor of the power inverter 1208. In the embodiment of FIG. 12, a separate inductor component has been eliminated from the inverter 1208. The leakage inductance of the rotary transformer 1202 is coupled to and used as part of the resonant network of the resonant inverter 1208. For example, the resonant network is formed by selecting a size for the capacitors 1210 and 1211 based on an amount of the leakage inductance of the rotary transformer 1202.

Figure 13:
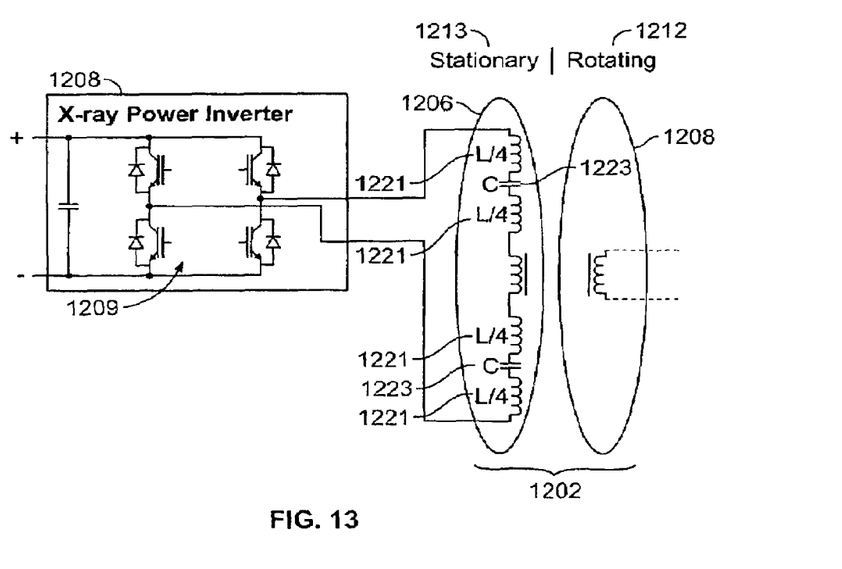
FIG. 13 is a schematic view of a contactless power transfer system in accordance with an embodiment.

In still another alternative embodiment shown in FIG. 13, the rotary transformer 1202 is provided with inductors 1221 and capacitors 1223 in series with one another. The inductors 1221 and capacitors 1223 are configured directly within the primary windings 1206 of the rotary transformer 1202, thus reducing the magnitude of the voltage experienced thereby. For example, for a one turn primary winding 1206, the capacitors 1221 may be placed at 180 degrees from the winding inputs, thereby minimizing the voltage experienced y the windings for the configuration of two resonant capacitors. This capacitor placement limits the resonant voltage developed by leakage inductance L. This configuration is exemplary only, and the particular configuration may be varied for different numbers of capacitors and primary turns for the purpose of reducing winding voltage.

Through the use of the above described multichannel, contactless power transfer system, the elimination of all contact slip ring brushes, associated dust, wear-out, and preventive maintenance needed results in advantageous cost savings. Furthermore, the removal of the x-ray power inverter assembly and bracket results in a direct reduction in the mass of from rotating frame of the system. Correspondingly, there is also a counter-balance of equal weight that may also be removed from the rotating frame. With both the inverter and counter-balance removed, there is further room to eliminate cantilevered components so as to have a much more uniformly balanced gantry, thereby facilitating the achievement of a faster gantry speech. Still a further cost reduction stems from the placement of the inverter(s) and auxiliary DC-DC converters on the stationary side of the frame.

Moreover, by having multiple secondary windings on the rotary transformer results there is a further reduction in the complexity, number of parts, and volume of the system. In addition, the system provides reduced radiated electromagnetic emissions as a result of the split impedance in the inverter output legs and the configuration of the E-shaped rotary transformer core.

The above-described fast rotation speed scanners may provide a cost-effective and highly reliable system. Various embodiments of a fast rotation speed scanner may include a gantry mechanism that rotates at speeds greater than gantrys current medical, industrial, and baggage imaging systems. The faster rotational speeds may result in part from relocating heavy components from the rotational gantry to the stationary portion of the scanner. Additionally, other lighter components may be placed on the rotatable gantry to provide additional features and facilitate cost-effective and reliable operation of the scanner.

While the invention has been described in terms of various specific embodiments, those skilled in the art will recognize that the invention can be practiced with modification within the spirit and scope of the claims.

What is claimed is:

1. An imaging system, comprising:
a gantry having a stationary member coupled to a rotating member, the rotating member having an opened area proximate an axis about which the rotating member rotates;
an x-ray source provided on the rotating member;
a resonant inverter to control an input voltage to the x-ray source;
an x-ray detector disposed on the rotating member and configured to receive x-rays from the x-ray source;
a rotary transformer having circumferentially disposed primary and secondary windings, the primary winding being disposed on the stationary member, and the secondary winding being disposed on the rotating member; and
a high voltage tank provided on the stationary member.

2. The imaging system of claim 1 wherein a resonant network is formed by a capacitor, provided along an output leg of the resonant inverter, coupled in series with a leakage inductance of the rotary transformer.

3. The imaging system of claim 1 comprising a detector including a first region of detector elements having a first size and a second region having detector elements having a second size wherein the first size is different than the second size such that the first region resolution is different than the second region resolution based on the respective element size in each region.

4. The imaging system of claim 1 wherein the resonant inverter is provided on the stationary member.

5. The imaging system of claim 1 comprising a plurality of x-ray sources provided on the rotating member, wherein a first of the plurality of x-ray sources comprises a first x-ray tube operating at a first voltage and a second of the plurality of x-ray sources comprises a second x-ray tube operating at a second voltage, wherein the first and second voltages are different.

6. The imaging system of claim 1 wherein the x-ray source comprises a plurality of x-ray sources provided on the rotating member, wherein a first of the plurality of x-ray sources comprises a first filter configured to permit x-rays having a first energy spectrum to pass therethrough and a second of the plurality of x-ray sources comprises a second filter configured to permit x-rays having a second energy spectrum to pass therethrough, wherein the first and second energy spectrums are different.

7. The imaging system of claim 1 comprising a plurality of x-ray detectors disposed on the rotating member.

8. The imaging system of claim 7 configured to perform acquisition of multiple scout scans simultaneously.

9. The imaging system of claim 7 wherein said detectors comprise a plurality of detector rows in a z-direction and wherein said detectors are shifted in a z-direction with respect to each other at least one of greater than one row to facilitate an increased axial coverage of the system in the z-direction and less than one row to facilitate a resolution of an acquired image.

10. The imaging system of claim 7 wherein an axial position of at least one detector is movable with respect to another of the plurality of detectors such that the detectors are positionable at least one of in substantial z-axial alignment to facilitate increasing a temporal resolution of the system, shifted z-axially less than one detector row to facilitate system spatial resolution, and shifted z-axially greater than one detector row to facilitate greater coverage in the z-direction.

11. The imaging system of claim 10 wherein an axial position of at least one detector is automatically movable with respect to another of the plurality of detectors at least one of between scans and during scans.

12. The imaging system of claim 1 wherein said detector comprises at least one of an integrating detector, a photon counting detector, an energy discriminating detector, and a backscatter detector.

13. The imaging system of claim 1 further configured to wobble a focal spot of the x-ray source using at least one of a movable pre-patient collimator, an x-ray tube comprising two focal spots on a single anode, and an x-ray tube comprising a plurality of emission sources such that the emission sources are alternately strobed.

14. The imaging system of claim 13 further comprising a focal spot monitor configured to monitor a position of the focal spot.

15. The imaging system of claim 1 comprising a plurality of rotary transformers comprising a primary winding that is magnetically coupled to at least one secondary winding, each secondary winding providing power to a respective rotary member subsystem.

16. The imaging system of claim 15 wherein at least one said secondary winding is configured to be magnetically coupled to the primary winding after initial manufacture such that retrofit components added to the rotating member after initial manufacture of the system are supplied with power.

17. The imaging system of claim 1 wherein said x-ray source comprises an x-ray tube having a plurality of independently controlled tube voltages.

18. The imaging system of claim 1 wherein said rotary transformer is configured to supply power to at least one of a high power x-ray tube and a plurality of x-ray tubes.

19. An imaging system, comprising:
a gantry having a stationary member coupled to a rotating member, the rotating member having an opened area proximate an axis about which the rotating member rotates;
a plurality of x-ray sources provided on the rotating member, a first x-ray source comprising an x-ray tube of a first type and a second x-ray source comprising an x-ray tube of a second type wherein the first and second types are different;
a resonant inverter to control an input voltage to the x-ray sources;
a plurality of x-ray detectors disposed on the rotating member and configured to receive x-rays from at least one of the x-ray sources, a first x-ray detector comprising an x-ray detector of a first type and a second x-ray detector comprising an x-ray detector of a second type wherein the first and second types are different;
a rotary transformer having circumferentially disposed primary and secondary windings, the primary winding being disposed on the stationary member, and the secondary winding being disposed on the rotating member; and
a high voltage tank provided on the stationary member.

20. The imaging system of claim 19 comprising a low power micro-focus x-ray tube and a respective high resolution detector.

21. The imaging system of claim 19 comprising a high power tube and a respective energy discriminating detector.

22. The imaging system of claim 19 comprising a detector including a first region of detector elements having a first size and a second region having detector elements having a second size wherein the first size is different than the second size such that the first region resolution is different than the second region resolution based on the respective element size in each region.

23. The imaging system of claim 19 comprising real-time feedback to at least one of the resonant inverter and at least one of the x-ray tubes using at least one of a real-time dosimeter, a scatter detector, and an x-ray detector element.

24. The imaging system of claim 19 further comprising a second modality detector including at least one of a PET detector, a SPECT detector, a gamma camera, and a baggage scanning specific detector comprising at least one of a neutron detector and a gamma detector.

25. The imaging system of claim 24 wherein said second modality detector is substantially aligned in a z-direction with at least one x-ray detector.

26. The imaging system of claim 24 a wherein resonant network is formed by a capacitor, provided along an output leg of the resonant inverter, coupled in series with a leakage inductance of the rotary transformer.

27. The imaging system of claim 24 wherein the rotating member is configured to receive luggage and the x-ray sources configured to perform baggage scanning.

28. A gantry mechanism, comprising: a stationary member;
a rotating member rotatably coupled to said stationary member, the rotating member having an opened area proximate an axis about which the rotating member rotates;
an x-ray source provided on the rotating member;
a resonant inverter to control an input voltage to the x-ray source;
an x-ray detector disposed on the rotating member and configured to receive x-rays from the x-ray source; and
a rotary transformer having circumferentially disposed primary and secondary windings, the primary winding being disposed on the stationary member and the secondary winding being disposed on the rotating member, said secondary windings coupled to a high voltage tank that is provided on the stationary member.

29. The gantry mechanism of claim 28 wherein the detector includes a first region of detector elements having a first size and a second region having detector elements having a second size wherein the first size is different than the second size such that the first region resolution is different than the second region resolution.

30. The gantry mechanism of claim 28 comprising a plurality of x-ray sources provided on the rotating member.

31. The gantry mechanism of claim 30 wherein a first of the plurality of x-ray sources comprises a first x-ray tube operating at a first voltage and a second of the plurality of x-ray sources comprises a second x-ray tube operating at a second voltage, wherein the first and second voltages are different.

32. The gantry mechanism of claim 28 comprising a plurality of x-ray detectors disposed on the rotating member.

33. The gantry mechanism of claim 32 configured to perform acquisition of multiple scout scans simultaneously using a plurality of said x-ray source and said plurality of x-ray detectors.

34. The gantry mechanism of claim 32 wherein said detectors comprise a plurality of detector rows in a z-direction and wherein said detectors are shifted in the z-direction with respect to each other at least one of greater than one row to facilitate an increased axial coverage of the mechanism in the z-direction and less than one row to facilitate a resolution of an acquired image.

35. The gantry mechanism of claim 32 wherein an axial position of at least one detector is movable with respect to another of the plurality of detectors such that the detectors are positionable at least one of in substantial z-axial alignment to facilitate increasing a temporal resolution of the mechanism, shifted z-axially less than one detector row to facilitate system spatial resolution, and shifted z-axially greater than one detector row to facilitate greater coverage in the z-direction.

36. The gantry mechanism of claim 35 wherein an axial position of at least one detector is automatically movable with respect to another of the plurality of detectors at least one of between scans and during scans based on a determined scan protocol.

37. A gantry mechanism, comprising:
a stationary member;
a rotating member rotatably coupled to said stationary member, the rotating member having an opened area proximate an axis about which the rotating member rotates;
an x-ray source provided on the rotating member;
a resonant inverter to control an input voltage to the x-ray source;
an x-ray detector disposed on the rotating member and configured to receive x-rays from the x-ray source; and
a rotary transformer having a circumferentially disposed primary winding and a plurality of circumferentially disposed secondary windings complementary to the primary winding, the primary winding being disposed on the stationary member and the secondary windings being disposed on the rotating member, each secondary winding providing power to a respective rotary member subsystem.

38. The gantry mechanism of claim 37 further configured to wobble a focal spot of the x-ray source using at least one of a movable pre-patient collimator, an x-ray tube comprising two focal spots on a single anode, and an x-ray tube comprising a plurality of anodes such that the anodes are alternately strobed.

39. The gantry mechanism of claim 38 further comprising a focal spot monitor configured to monitor a position of the focal spot.

40. The gantry mechanism of claim 37 wherein at least one of said plurality of secondary windings is configured to be magnetically coupled to the primary winding after initial manufacture such that retrofit components added to the rotating member after initial manufacture of the mechanism are supplied with power.

41. The gantry mechanism of claim 37 wherein said x-ray source comprises an x-ray tube having a plurality of independently controlled tube voltages.

42. The gantry mechanism of claim 37 wherein said rotary transformer is configured to supply power to at least one of a high power x-ray tube and a plurality of x-ray tubes.

* * * * *